United States Patent
Chai et al.

(10) Patent No.: US 11,719,701 B2
(45) Date of Patent: Aug. 8, 2023

(54) BLOOD GLUCOSE LEVEL MEASURING CHIP AND BLOOD GLUCOSE LEVEL MEASURING DEVICE SET

(71) Applicant: TERUMO KABUSHIKI KAISHA, Tokyo (JP)

(72) Inventors: Fumihiko Chai, Yamanashi (JP); Takeyuki Moriuchi, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 193 days.

(21) Appl. No.: 16/717,383

(22) Filed: Dec. 17, 2019

(65) Prior Publication Data

US 2020/0124610 A1 Apr. 23, 2020

Related U.S. Application Data

(63) Continuation of application No. PCT/JP2018/021676, filed on Jun. 6, 2018.

(30) Foreign Application Priority Data

Jul. 14, 2017 (JP) .................................. 2017-137932

(51) Int. Cl.
- *C12Q 1/32* (2006.01)
- *G01N 33/66* (2006.01)
- *G01N 21/78* (2006.01)

(52) U.S. Cl.
CPC ............... *G01N 33/66* (2013.01); *C12Q 1/32* (2013.01); *G01N 21/78* (2013.01)

(58) Field of Classification Search
CPC ........ G01N 33/66; G01N 21/78; G01N 21/01; C12Q 1/32; C12M 1/34
See application file for complete search history.

(56) References Cited

U.S. PATENT DOCUMENTS

2004/0136871 A1 7/2004 Pachl et al.
2006/0035300 A1 2/2006 Yamaoka et al.
(Continued)

FOREIGN PATENT DOCUMENTS

CN 1662660 A 8/2005
CN 101238374 A 8/2008
(Continued)

OTHER PUBLICATIONS

Pubchem, n-Ethyl-n-(2-hydroxy-3-sulfopropyl)-3,5- dimethylaniline sodium salt monohydrate (Year: 2023).*
The extended European Search Report dated Nov. 25, 2020, by the European Patent Office in corresponding European Patent Application No. 18832002.2-1118. (7 pages).
(Continued)

*Primary Examiner* — Matthew D Krcha
*Assistant Examiner* — Sophia Y Lyle
(74) *Attorney, Agent, or Firm* — Buchanan Ingersoll & Rooney PC

(57) ABSTRACT

A blood glucose level measuring chip exhibits excellent blood spreading ability and can maintain a reaction rate of blood with a reagent, even where the blood has a high hematocrit value (Ht). The blood glucose level measuring chip includes a blood glucose level measuring reagent including a supply port through which blood is supplied, a flow path having the supply port formed at one end of the flow path, and a blood glucose level measuring reagent containing an aromatic hydrocarbon having at least one sulfonic acid group disposed on an inner wall defining the flow path, wherein a ratio A/B is 3.7 mmol/L or more to 184.8 mmol/L when A (mmol) represents the total molar amount of aromatic hydrocarbons contained in the blood glucose level measuring reagent, and B (L) represents a volume of a region in which the blood glucose level measuring reagent and the blood are dissolved.

20 Claims, 5 Drawing Sheets

(56) References Cited

U.S. PATENT DOCUMENTS

| | | | |
|---|---|---|---|
| 2010/0075352 A1 | 3/2010 | Umegae et al. | |
| 2013/0161204 A1* | 6/2013 | Uchiyama | C12Q 1/26 435/26 |
| 2016/0131590 A1 | 5/2016 | Kim | |

FOREIGN PATENT DOCUMENTS

| | | | |
|---|---|---|---|
| EP | 0160847 A1 * | 11/1985 | ........... G01N 33/526 |
| JP | 2006215034 A | 8/2006 | |
| JP | 2008197077 A * | 8/2008 | |
| JP | 2008197077 A | 8/2008 | |
| JP | 4381463 B2 | 11/2008 | |
| JP | 2011185744 A * | 9/2011 | |
| WO | 2006/023927 A1 | 3/2006 | |
| WO | 2014049704 A1 | 4/2014 | |
| WO | WO-2014049704 A1 * | 4/2014 | ........ B01L 3/502746 |
| WO | 2016152225 A1 | 9/2016 | |
| WO | WO-2016152225 A1 * | 9/2016 | |
| WO | 2017134878 A1 | 8/2017 | |

OTHER PUBLICATIONS

International Search Report (PCT/ISA/210) dated Sep. 4, 2018, by the Japan Patent Office as the International Searching Authority for International Application No. PCT/JP2018/021676.

Written Opinion (PCT/ISA/237) dated Sep. 4, 2018, by the Japan Patent Office as the International Searching Authority for International Application No. PCT/JP2018/021676.

An English Translation of the International Search Report (Form PCT/ISA/210) and the Written Opinion of the International Searching Authority (Form PCT/ISA/237) dated Sep. 4, 2018, by the Japanese Patent Office in corresponding International Application No. PCT/JP2018/021676. (11 pages).

Zhou et al., "Highly Sensitive and Multi-Parameter Optical Detection for Whole Blood on Centrifugal Microfluidic Chip", Optics and Precision Engineering, (Nov. 2013), vol. 21, No. 11, pp. 2821-2828.

Office Action (The First Office Action) dated Mar. 16, 2022, by the State Intellectual Property Office of People's Republic of China in corresponding Chinese Patent Application No. 201880009487.6 and an English Translation of the Office Action. (12 pages).

* cited by examiner

FIG. 6(a)
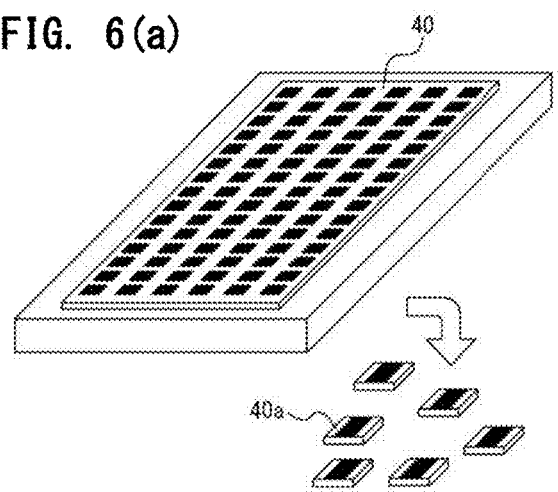
FIG. 6(b)
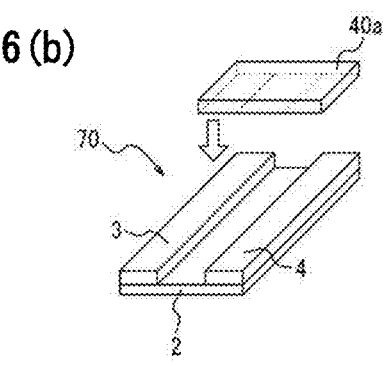
FIG. 6(c)
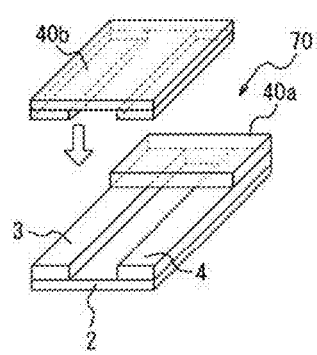
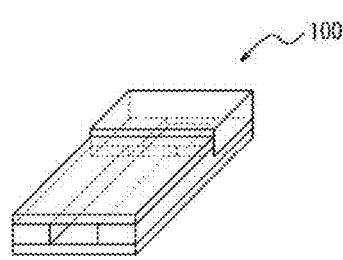
FIG. 6(d)

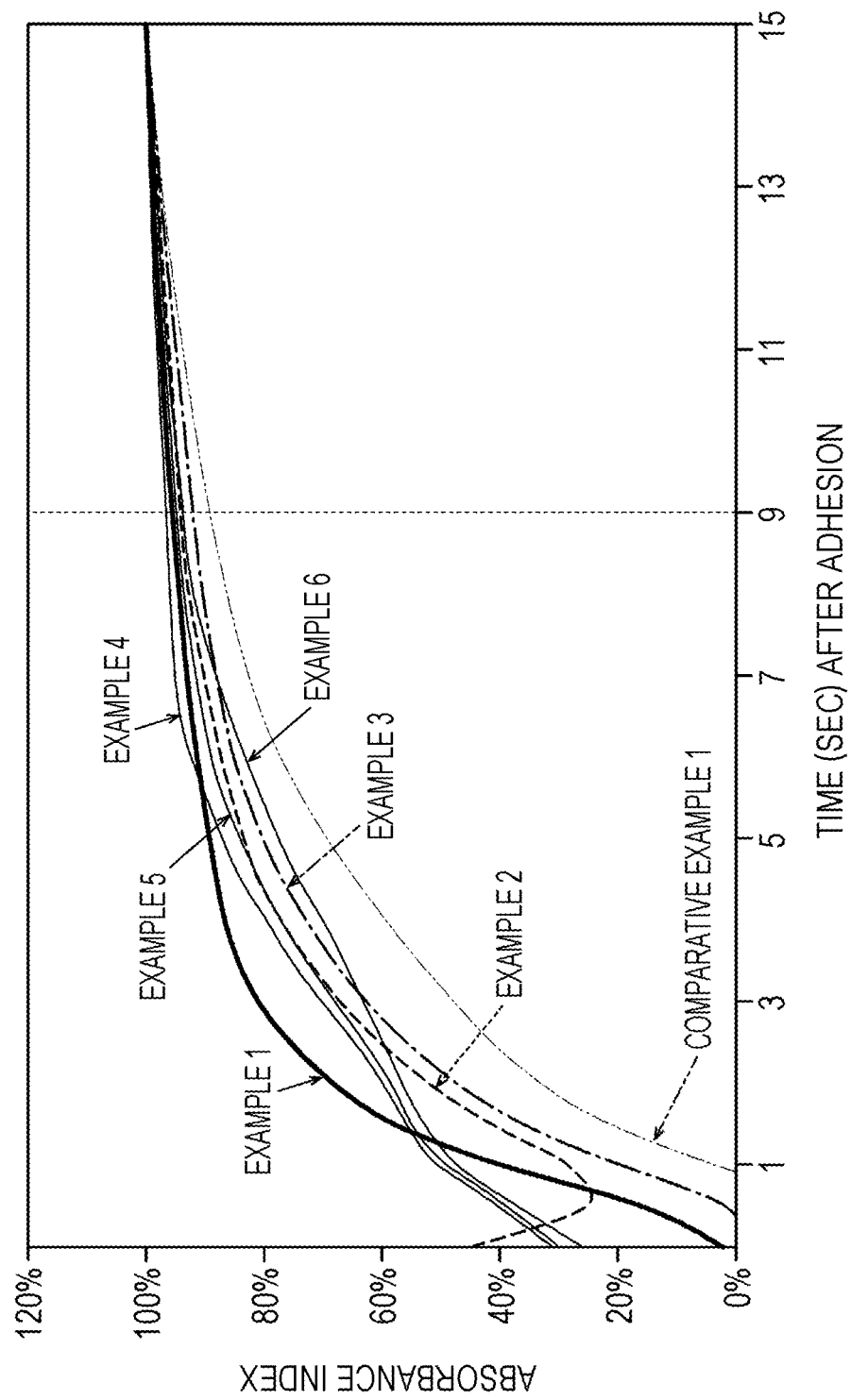

BLOOD GLUCOSE LEVEL MEASURING CHIP AND BLOOD GLUCOSE LEVEL MEASURING DEVICE SET

CROSS-REFERENCES TO RELATED APPLICATIONS

This application is a continuation of International Application No. PCT/JP/2018/021676 filed on Jun. 6, 2018, and claims priority to Japanese Application No. 2017-137932 filed on Jul. 14, 2017, the entire contents of which is incorporated herein by reference.

TECHNICAL FIELD

The present disclosure relates to a blood glucose level measuring chip and blood glucose level measuring device set, and for example, a blood glucose level measuring chip which is excellent in blood spreading and may maintain a reaction rate of blood with a reagent, even in a case where the blood with a high hematocrit value (Ht) is supplied, and the blood glucose level measuring device set including the blood glucose level measuring chip.

BACKGROUND DISCUSSION

A blood glucose level measuring device has been broadly used to measure glucose in blood (see, e.g., JP 2006-215034 A).

Such a glucose level measuring device, when the blood (whole blood) is attached to the blood glucose level measuring chip having reagents including, for example, an enzyme and a chromogenic indicator (see, e.g., JP 4381463 B2), optically measures a degree of coloring resulting from the reaction of the blood (whole blood) with the reagent to measure the glucose component in the blood (see, e.g., WO 2014/049704 A).

In the case where the blood glucose level measuring device is used in the measurement of the blood glucose level as described above, it can be desirable for the blood sample amount to be small to alleviate the suffering of a patient. In order to reduce the blood sample amount, it can be desirable to narrow the blood flow path in the blood glucose level measuring chip (to render cross-sectional area of the blood flow path small).

SUMMARY

In the blood glucose level measurement using the blood glucose level measuring device as described above, a blood glucose level measuring reagent having high solubility in blood can be used. However, when blood having a high hematocrit value (Ht) is supplied to a blood glucose level measuring chip having a narrow blood flow path, it is difficult to control the mixing and dissolution of the blood flowing in the flow path and the blood glucose level measuring reagent, depending on the environmental temperature. As a result, air to be pushed with the inflowing blood and then discharged is not discharged from the blood glucose level measuring chip. In addition, air (air bubbles) may remain in the measurement part (reagent part) of the blood glucose level measuring chip because air is taken into the inflowing blood. Particularly, there has been a problem in that the blood glucose level may not be accurately measured under heating or in a high temperature environment in the summer.

The present disclosure provides a blood glucose level measuring chip which is excellent in blood spreading and is capable of maintaining a reaction rate of blood with a reagent, even in a case where blood having a high hematocrit value (Ht) is supplied, and a blood glucose level measuring device set including the blood glucose level measuring chip.

According to a first exemplary aspect of the present disclosure, a blood glucose level measuring chip includes a supply port through which blood is supplied, a flow path having the supply port formed at one end of the flow path, and a blood glucose level measuring reagent disposed on an inner wall defining the flow path, and may be installed in the device for measuring the glucose level in the blood, the blood glucose level measuring reagent contains an enzyme of which a substrate is glucose, a chromogenic indicator, and an aromatic hydrocarbon having at least one sulfonic acid group, and a ratio A/B is 3.7 mmol/L to 184.8 mmol/L when A (in mmol) represents the total mole number of aromatic hydrocarbons contained in the reagent and B (in liters, L) represents a volume of a region in which the blood glucose level measuring reagent and blood are dissolved.

For example, even in a case where blood having a high hematocrit value (Ht) is supplied, it is possible to provide a blood glucose level measuring chip which is excellent in blood spreading and is capable of maintaining the reaction rate between blood and a reagent.

In the present specification, the term "aromatic hydrocarbon" is defined as a cyclic compound containing only carbon atoms in the ring of the cyclic compound. The term "aromatic hydrocarbon" does not encompass a heterocyclic compound, and is a compound that has no amine.

In addition, "the region in which the blood glucose level measuring reagent and the blood are dissolved (for example, region X in FIG. 2)" refers to "a gap (e.g., gap X in FIG. 2) which is placed between a part on which the blood glucose level measuring reagent is formed (e.g., reagent formed surface 1a in FIG. 2) and an opposing part (e.g., opposing surface 2a in FIG. 2) facing the blood glucose level measuring reagent in a thickness direction of the blood glucose level measuring reagent, on an inner wall defining the flow path."

In one embodiment of the present disclosure, the A/B ratio is, for example, 3.7 mmol/L to 123.3 mmol/L, for example, 3.7 mmol/L to 61.6 mmol/L, for example, 3.7 mmol/L to 15.0 mmol/L.

For example, setting the A/B ratio to be 3.7 mmol/L to 123.3 mmol/L can provide the blood glucose level measuring chip which is excellent in the blood spreading and is capable of maintaining the reaction rate of the blood with the reagent, even in a case where any Ht blood within the range of Ht20 and Ht70 is supplied.

In addition, setting the A/B ratio to be 3.7 mmol/L and 61.6 mmol/L can provide the blood glucose level measuring chip which is excellent in the blood spreading and is capable of maintaining the reaction rate of the blood with the reagent, even in a case where any Ht blood within the range of Ht0 and Ht70 is supplied.

Furthermore, setting the A/B ratio to be 3.7 mmol/L to 15.0 mmol/L can provide the blood glucose level measuring chip which is more excellent in the blood spreading and is capable of further maintaining the reaction rate of the blood with the reagent.

In one embodiment of the present disclosure, it is exemplary that the aromatic hydrocarbon has two or more sulfonic acid groups.

For example, at least one sulfonic acid group can be present as a substituent on the aromatic ring of the aromatic hydrocarbon. For example, by disposing at least one sulfonic acid group on the aromatic ring, the reagent can be easily wetted by the blood (easy for mixing).

For example, as the aromatic hydrocarbon, disodium 1,3-benzene disulfonate or trisodium naphthalene-1,3,6-trisulfonate is exemplary.

In addition, for example, 1,3-benzenedisulfonic acid disodium and trisodium naphthalene-1,3,6-trisulfonate do not have a buffering capacity. The buffer component contained in the blood has sufficient buffering capacity necessary for the blood glucose level measuring reagent and blood to react with each other. Therefore, the pH of the mixture of the blood glucose level measuring reagent and the blood can be maintained over the period of the reaction without adding a buffer to the blood glucose level measuring reagent.

In one embodiment of the present disclosure, it is exemplary that the molar ratio of the coloring reagent and the aromatic hydrocarbon compound (color developing reagent: aromatic hydrocarbon compound) in the blood glucose level measuring reagent be in the range of 1:0.07 to 1:7.4. If the blood glucose level measuring reagent is used within the range of the molar ratio above, the blood spreading in the blood glucose level measuring chip can be improved.

In one embodiment of the present disclosure, it is exemplary to further include a tetrazolium salt as the coloring reagent.

According to a second exemplary aspect of the present disclosure, a blood glucose level measuring device set includes the blood glucose level measuring chip as a first aspect of the present disclosure and a blood glucose level measuring device for measuring a blood glucose level in blood, wherein the blood glucose level measuring device includes an irradiation part for irradiating the reaction product of the blood and the reagent with light, a light receiving part for receiving the measurement light transmitted through the reaction product, the measurement light absorbed by the reaction product, or the measurement light reflected from the reaction product, and a processing section for processing the signal obtained from the measurement light.

The present disclosure can provide a blood glucose level measuring chip which is excellent in a blood spreading and is capable of maintaining a reaction rate of blood with a reagent, even in a case where blood having a high hematocrit value (Ht) is supplied, and a blood glucose level measuring device set including the blood glucose level measuring chip.

BRIEF DESCRIPTION OF THE DRAWINGS

FIGS. 6(a) to 6(d) are views for describing a method for preparing the blood glucose level measuring chip of FIG. 1.

FIG. 7 is a graph representing a color developing rate of each reagent (Examples 1 to 6 and Comparative Example 1), in which a vertical axis shows an absorbance index (the indicator when a color developing amount after 15 seconds is set to 100%: %) and an horizontal axis shows a time (seconds) after being attached.

DETAILED DESCRIPTION (Blood Glucose Level Measuring Chip)

An exemplary blood glucose level measuring chip according to the present disclosure is described in detail below.

Figure 1:
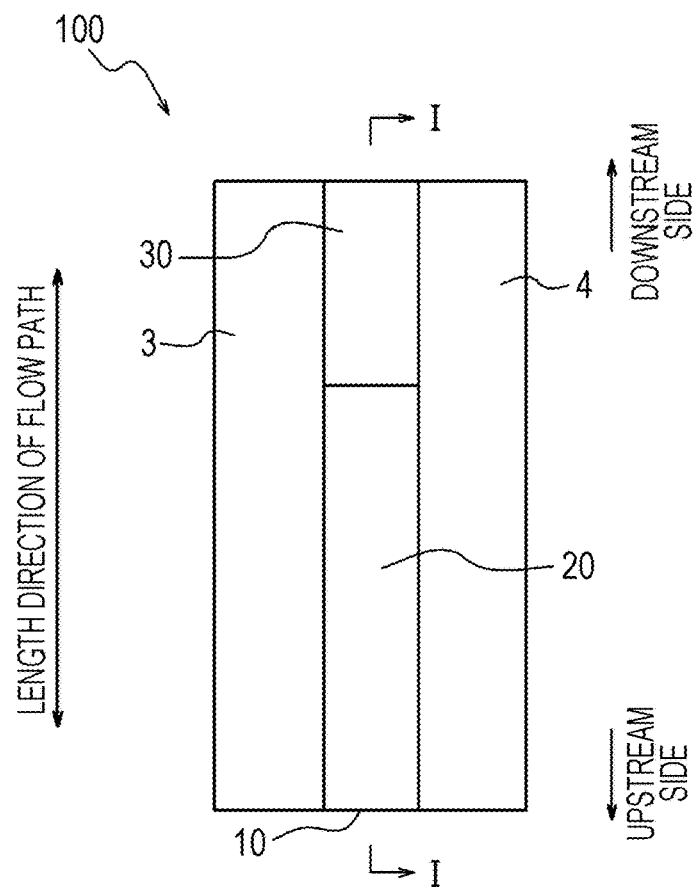
FIG. 1 is a plan view showing a blood glucose level measuring chip according to an exemplary embodiment of the present disclosure.
Figure 2:
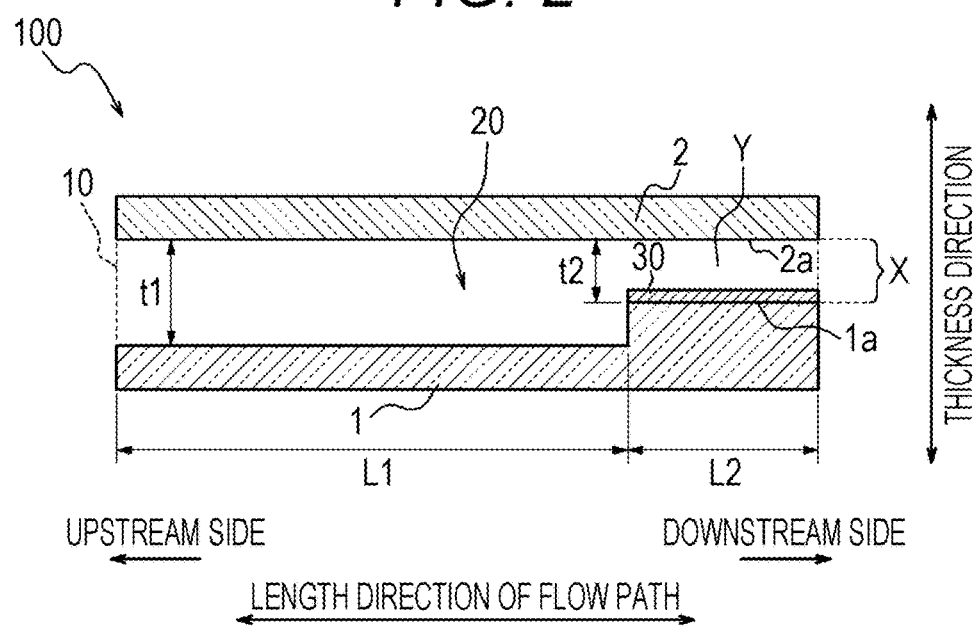
FIG. 2 is a cross-sectional view taken along line I-I shown in FIG. 1.

FIG. 1 is a plan view showing a blood glucose level measuring chip according to an embodiment of the present disclosure. In addition, FIG. 2 is a cross sectional view taken along line I-I shown in FIG. 1. In addition, FIG. 3 illustrates a flow path in the blood glucose level measuring chip of FIG. 1.

Figure 3:
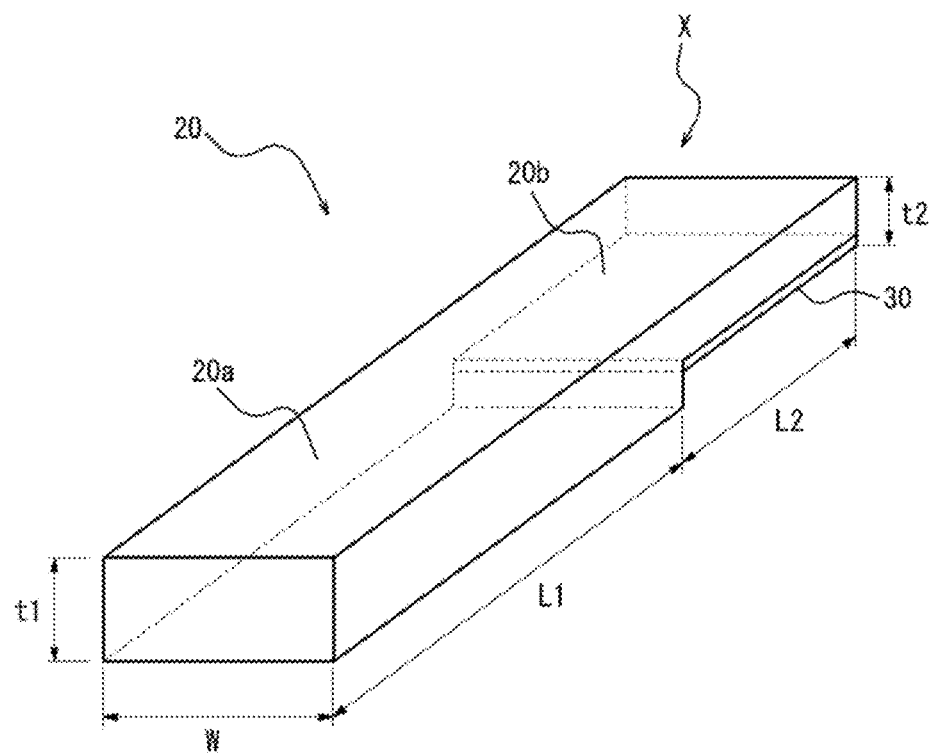
FIG. 3 is a view for describing a flow path in the blood glucose level measuring chip of FIG. 1.

As shown in FIGS. 1, 2, and 3, the blood glucose level measuring chip 100 according to the present embodiment includes a supply port 10, a flow path 20, and a reagent layer 30 and may be mounted on the blood glucose level measuring device as described below.

Each of the members of the blood glucose level measuring chip 100 according to the present embodiment and the features constituted by the respective members is described in detail below.

<Supply port 10, flow path 20, and reagent layer 30>

As shown in FIGS. 1, 2 and 3, the blood glucose level measuring chip 100 includes a first base 1 forming a bottom surface part, a second base 2 forming a top surface part, and adhesive parts 3 and 4 which are installed between a first base 1 and a second base 2 and at both ends in the width direction orthogonal to the chip thickness direction.

As such, in adhesive parts 3 and 4, the first base 1 and the second base 2 are adhered to each other with a state of the spacer having an arbitrary thickness being inserted (not shown) between the first base 1 and the second base 2, and a pore of a predetermined size is formed between the first base 1 and the second base 2. The pore of the predetermined size is formed as the flow path 20 from the first end portion to the second end portion of the blood glucose level measuring chip 100. The supply port 10 is provided on the first end side (upstream side) of the flow path 20. The user attaches the blood of 0.3 μL to 3 μL to supply port 10 and the blood flows into the blood glucose level measuring chip 100 via the capillarity. The blood glucose level measuring reagent is applied on the second end side of the flow path 20. More specifically, in the second end side, the reagent layer 30 made of the blood glucose level measuring reagent is installed on at least a part of at least one surface (reagent formed surface 1a), on the inner wall defining the flow path 20. The reagent layer 30 can be provided over the entire surface of the reagent formed surface 1a. For example, the reagent layer 30 is applied so as to cover at least 50% or more of the area of the reagent formed surface 1a. In the flow path 20, a space Y is defined directly above the reagent formed surface 1a and the reagent layer 30. The cross-sectional shape of the flow path 20 can be a rectangle, a square, a circle, or an ellipse. The volume of the flow path 20 can be 0.0003 to 0.003 cm$^3$, for example, 0.0004 to 0.0015 cm$^3$. The volume of the space Y in the flow path 20 can be 0.00003 to 0.001 cm$^3$, for example, 0.00005 to 0.0003 cm$^3$. The blood glucose level measuring chip 100 may be provided with a vent port at any position on the downstream side (the side opposite to the supply port 10 on the flow path 20) with respect to the position of the supply hole 10 in order to promote the movement of blood in the flow path 20. For example, the space Y does not include a space which forms a vent port. When the vent port is installed at the second base 2, one or a plurality of pores may be provided so as to communicate from the external space of the blood glucose level measuring chip 100 to the space Y of the flow path 20. When the vent port is not installed at the second base 2, the vent hole is provided on the second end side (that is, the downstream side of the space Y) with respect to the reagent layer 30. For example, a porous member or a filter may be disposed in the vent port to prevent leakage of blood. Alternatively, a narrow flow path extending from the space Y may be further provided on the downstream side of the reagent part to form a vent port. For example, the leakage of blood may be prevented by performing water repellent processing or the like on the first base 1 and/or the second base 2 forming the vent port.

The material of the first base 1 may be appropriately selected in accordance with the purpose (light irradiation/light reception), and examples of the material include polyethylene terephthalate (PET), polymethylmethacrylate, polystyrene, cyclic polyolefin, cyclic olefin copolymer, transparent organic resin materials such as polycarbonate and polydimethyl siloxane; transparent inorganic materials such as glass and quartz; and the like.

The material of the second base 2 can be appropriately selected in accordance with the purpose (light irradiation/light reception), and for example, may be a transparent organic resin material such as a hydrophilic polyester film (3M hydrophilicized film, tesa (registered trademark) 62580), ARflow (registered trademark) 93210, ARflow (registered trademark) 93127), and the like.

The thicknesses of the adhesive parts 3 and 4 are appropriately adjusted in order to set the distance in the chip thickness direction of the flow path 20 to a desired value. For example, after a spacer having an arbitrary thickness is disposed between the first base 1 and the second base 2, and they may be bonded or fused. Alternatively, the adhesive member may also serve as a spacer by using a double-sided tape having a predetermined thickness as an adhesive member for bonding the first base 1 and the second base 2. The adhesive parts 3 and 4 can be installed in line symmetry with respect to the center line of the flow path 20 so that blood flows uniformly through the flow path 20.

In the case that A (in mmol) is a total mole number of aromatic hydrocarbons contained in the blood glucose level measuring reagent of the reagent layer 30, which will be described later, and B (in liters, L) is a volume (reagent length L2× width W× thickness t2) of a region X in which the blood glucose level measuring reagent and blood are dissolved (the gap X introduced between the reagent formed surface 1a on which the reagent layer 30 made of the reagent for measuring a blood glucose level is formed, and the opposing surface 2a facing the reagent layer 30 in the thickness direction of the reagent layer 30, on the inner wall defining the flow path 20), the A/B ratio is not particularly limited and, for example, can be 3.7 mMmmol/L to 184.8 mmol/L, for example, 3.7 mmol/L to 123.3 mmol/L, for example, 3.7 mmol/L to 61.6 mmol/L, for example, 3.7 mmol/L to 15.0 mmol/L. For example, when the A/B ratio is 3.7 mmol/L to 184.8 mmol/L, excellent blood spreading can be obtained and the reaction rate of the blood with the reagent can be maintained.

For example, setting the A/B ratio to be 3.7 mmol/L to 123.3 mmol/L may obtain excellent blood spreading, and maintain the reaction rate of the blood with the reagent, even in a case where blood of any Ht within the range of Ht20 to Ht70 is supplied.

For example, setting the A/B ratio to be 3.7 mmol/L to 61.6 mmol/L may obtain excellent blood spreading, and maintain the reaction rate of the blood with the reagent, even in a case where blood of any Ht within the range of Ht0 to Ht70 is supplied.

For example, setting the A/B ratio to be 3.7 mmol/L to 15.0 mmol/L may obtain a better blood spreading and further maintain the reaction rate of blood with the reagent.

In addition, "the region X in which the blood glucose level measuring reagent and the blood are dissolved", that is, "gap X introduced between the reagent formed surface 1a on which the reagent layer 30 made of the blood glucose level measuring reagent is formed, and the opposing surface 2a facing the reagent layer 30 in the thickness direction of the reagent layer 30, on the inner wall defining the flow path 20 (region X including the space Y and region of the reagent layer 30 of FIG. 2)" refers to for example, "a gap existing in the flow path 20, having two surfaces of (i) a reagent formed surface 1a on which a reagent layer 30 is formed and (ii) a surface (opposing surface 2a) formed by an intersection of a vertical line passing through each point constituting the reagent formed surface 1a and perpendicular to the reagent formed surface 1a and the second base 2."

It is exemplary that the molar ratio of the coloring reagent and the aromatic hydrocarbon compound (coloring reagent: aromatic hydrocarbon compound) range from 1:0.07 to 1:7.4. If the blood glucose level measuring reagent is used within the range of the molar ratio above, the spreading of blood flowed into the blood glucose level measuring chip 100 can be improved. For example, "the spreading of blood flowed into the blood glucose level measuring chip" or "blood spreading" means that blood and blood glucose level measuring reagent which are flowing from the first end side to the second end side of the reagent layer 30 in the blood glucose level measuring chip, is uniformly mixed and dissolved when the blood is flowed into the spaces Y and X. Furthermore, "good spreading of the blood flowed into the blood glucose level measuring chip" means that when the blood flowing from the first end side to the second end side of the flow path 20 is mixed or dissolved with the blood glucose level measuring reagent, the flowing state of the blood is not disturbed, and the blood moves forward to the second end while being dissolved with the blood glucose level measuring reagent at a predetermined rate. The term "flowing state of the blood is not disturbed" includes a situation in which the tip of the inflowing blood flows uniformly through the flow path 20 in the flow path section. It is exemplary that the aromatic hydrocarbons be blended at a ratio of 1 pmol to 12 pmol per 1 U of the enzyme combined in the blood glucose level measuring reagent. The amount of the aromatic hydrocarbon (to be described later) contained in the blood glucose level measuring reagent of the reagent layer 30 that is added per the blood glucose level measuring chip, can be 0.238 (μg/chip) to 11.7 (μg/chip), for example, 0.238 (μg/chip) to 7.82 (μg/chip), for example, 0.238 (μg/chip) to 3.911 (μg/chip), for example, 0.238 (μg/chip) to 0.952 (μg/chip) as disodium salt of an aromatic hydrocarbon. The content ratio of the aromatic hydrocarbon or the added amount of the aromatic hydrocarbon per the blood glucose level measuring chip within any one of the above exemplary ranges may make a better blood spreading obtained, and at the same time, the reaction rate between the blood and the reagent maintained.

For example, when the blood passing through the flow path 20 flows into the space Y just above the reagent layer 30, the blood glucose level measuring reagent in the reagent layer 30 is rapidly dissolved in the blood. For example, the concentration of the aromatic hydrocarbon in the plasma, (which prior to being dissolved in the blood was contained in the blood glucose level measuring reagent in the reagent layer 30 to be described later) can be from 5.25 mmol/L to 308 mmol/L, for example, from 12.5 mmol/L to 205.3 mmol/L, for example, from 12.5 mmol/L to 50.0 mmol/L. The concentration of the aromatic hydrocarbon in the plasma within any of the above exemplary ranges may make a better blood spreading obtained and at the same time, the reaction rate between the blood glucose and the reagent more reliably maintained.

<<Method for Producing Reagent Layer 30>>

For example, the method for producing the reagent layer structure includes at least a coating step and a drying step, and includes other steps if desired.

—Application Process—

For example, the application process is a process of applying an application liquid (coating liquid) containing a blood glucose level measuring reagent to be described later.

The application process is not particularly limited and may be appropriately selected according to the purpose, and examples of the application process include a spray application process, an inkjet process, a screen printing process, and a gravure printing process. These may be used alone or in combination with two or more kinds.

—Drying Process—

For example, the drying process is a process of drying the applied coating liquid.

The drying temperature and the drying time in the drying process may be appropriately selected depending on the purpose.

<<Blood Glucose Level Measuring Reagent>>

For example, the blood glucose level measuring reagent contains at least an enzyme, a chromogenic indicator (indicator), and an aromatic hydrocarbon. In addition, the blood glucose level measuring reagent can include other components such as an electron acceptor (mediator), a transition metal salt and the like.

Also, as a blood glucose level measuring reagent, D-glucose and a coloring dye (for example, a tetrazolium salt such as WST-4 described later) in blood can be included and act by receiving an electron from an enzyme (for example, glucose dehydrogenase (GDH)). A pigment developing the color depending on the amount and concentration of the analyte can be included.

—Aromatic Hydrocarbon—

The aromatic hydrocarbon is not particularly limited and can be an aromatic hydrocarbon having at least one sulfonic acid group, and may be appropriately selected according to the purpose, and for example, may include benzenesulfonic (BS) sodium (see the following structural formula (1), disodium 1,3-benzene disulfonate (DSB) (see the following structural formula (2)), trisodium 1,3,5-benzene trisulfonate (see the following structural formula (3)), trisodium naphthalene-1,3,6-trisulfonate (TSN) (see the following structural formula (4)), and anthracene-1,3,6-trisulfonic trisodium (see the following structural formula (5)). These may be used alone or in combination with two or more kinds.

Among them, aromatic hydrocarbons having two or more sulfonic acid groups (for example, disodium 1,3-benzene disulfonate (DSB), trisodium naphthalene-1,3,6-trisulfonate (TSN)) are exemplary in view of the fact that the reaction rate of the blood with the blood glucose level measuring reagent can be further improved. The aromatic hydrocarbon is not easily dissolved in an aqueous liquid such as blood, but when the hydrogen in the aromatic hydrocarbon is substituted with a sulfonic acid group (ion), the aromatic hydrocarbon is likely to be dissolved in blood. Furthermore, substituting the aromatic hydrocarbon with a plurality of sulfonic acid groups makes the aromatic hydrocarbon easily dissolve in the blood, and at the same time, the interface performance is appropriately imparted. Therefore, for example, since the aromatic hydrocarbon has no hemolytic action which hemolyzes blood cells, it can be used for measurement in whole blood.

For example, when the aromatic hydrocarbon having two or more sulfonic acid groups is added to the blood glucose level measuring reagent, the reaction rate of the blood glucose level measuring reagent with the blood can be remarkably increased. This is because the affinity between the blood glucose level measuring reagent and blood is increased by combining an aromatic hydrocarbon having two or more sulfonic acid groups with the blood glucose level measuring reagent. In the blood glucose level measuring chip, the effect of the present disclosure may be remarkably obtained by adjusting the content of the aromatic hydrocarbons. That is, the blood glucose level measuring reagent of the dried state, which is applied to the blood glucose level measuring chip, and the blood are uniformly mixed and dissolved, and at the same time, the color development according to the amount of glucose in the blood may be rapidly obtained. Furthermore, even if the number of sulfonic acid groups contained in the aromatic hydrocarbon is increased, there is no adverse effect on the stability.

[Formula 1]

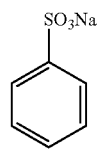

structural formula (1)

[Formula 2]

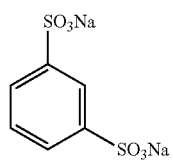

structural formula (2)

[Formula 3]

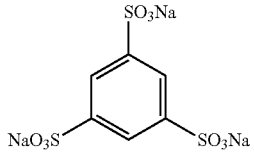

structural formula (3)

[Formula 4]

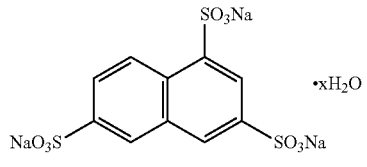

structural formula (4)

[Formula 5]

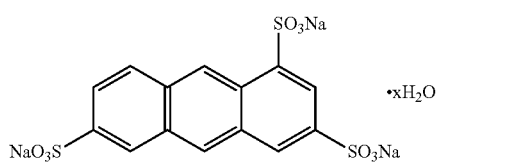

structural formula (5)

The molar number of aromatic hydrocarbons relative to 1 mol of the chromogenic indicator can be 0.07 mol to 7.4 mol. When the blood glucose level measuring reagent is used in the range of the molar ratio, the reaction rate of the blood adhered to the blood glucose level measuring chip with the blood glucose level measuring reagent can be advantageously improved. The molar number of aromatic hydrocarbons relative to 1 mol of the chromogenic indicator can be 0.075 mol to 7.4 mol. The molar number of aromatic hydrocarbons relative to 1 mol of the chromogenic indicator can be 0.075 mol to 3.7 mol. When the blood glucose level measuring reagent is used in the range of the molar ratio, a wide blood glucose level of 0 mg/dL to 1200 mg/dL may be measured, and also if the content of the aromatic hydrocarbon is one of the above exemplary ranges, it is possible to improve the blood spreading and reaction rate of the blood with the blood glucose level measuring reagent.

—Enzyme—

For example, the enzyme reacting with the glucose in blood plays a role to extract electrons from the glucose.

The enzyme is not particularly limited as long as the glucose is used as a substrate, and may be appropriately selected depending on the purpose, and examples of the enzyme include glucose dehydrogenase (GDH) and glucose oxidase (GOD). These may be used alone or in combination with two or more kinds.

Among these, flavin adenine dinucleotide (FAD)-dependent glucose dehydrogenase (GDH-FAD) is exemplary.

The pH region where the reaction of glucose dehydrogenase (GDH) proceeds smoothly (that is, the optimum pH region) is usually near neutral (about pH 6.5 to 7.3), but the proper pH region varies depending on the enzyme. The pH of the blood glucose level measuring reagent of the present disclosure is appropriately adjusted in consideration of the optimum pH of the enzyme to be used and the stability of the other components.

The concentration at the time of reacting the blood sample with the enzyme is not particularly limited and may be appropriately selected according to the target blood glucose level measuring range, and can be 1 U/μL or more, for example, 4 U/μL or more, for example, 8 U/μL to 20 U/μL.

If the concentration in the blood sample reaction is one of the above exemplary ranges, the reaction can be rapidly completed.

When the amount of the enzyme contained in the blood glucose level measuring reagent is E (MU: mega unit) and the volume of the gap X is B(L), the ratio E/B can be 2 (MU/L) or more, for example, 2 (MU/L) to 11 (MU/L).

When the ratio E/B is within an exemplary range, it is possible to rapidly measure the blood glucose level of a variety of concentration. When the ratio E/B is within an exemplary range, a variety of blood glucose level can be rapidly measured and storage stability is improved.

It is exemplary that the enzyme (1 U):aromatic hydrocarbon (pmol) be 1:1 to 1:12 as the mixing ratio of the enzyme contained in the blood glucose level measuring reagent.

—Chromogenic Indicator—

For example, the chromogenic indicator (oxidereduction coloring reagent) accepts (by the reduction) electrons or hydrogen peroxide generated by the reaction of the enzyme with the analyte, and develops color (changing color) depending on the amount and concentration of the analyte.

The chromogenic indicator is not particularly limited and may be appropriately selected depending on the purpose, and examples thereof may include tetrazolium salts (for example, tetrazolium salts (A), WST-4, WST-1, WST-5, MTS or MTT), sodium phosphorous molybdate, indigocarmine, dichloroindo phenol, resazurin, and the like. These may be used alone or in combination with two or more kinds.

Among them, a tetrazolium salt having a benzothiazolyl group is exemplary, and a tetrazolium salt having a solubility in water of 200 mmol/L or more is exemplary. As a result, the dissolution rate of the blood glucose level measuring reagent and the blood sample can be improved. Regarding the tetrazolium salt above, it is exemplary to use 2-(6-methoxy benzo thiazolyl)-3-(3-sulfo-4-methoxy-phenyl)-5-(2,4-disulfophenyl)-2H-tetrazolium salt (tetrazolium salt (A)), 2-(2-benzothiazolyl)-3-(4-carboxy-2-methoxyphenyl)-5-[4-[(2-sodio-sulfoethyl)carbamoyl]phenyl]-2H-tetrazol-3-ium (WST-4) because of its good coloring spectrum and high solubility in an aqueous liquid. As a result, for example, the solubility of the blood sample with the blood glucose level measuring reagent is good, and the high-precision detection can be achieved even in a case where the blood sample is whole blood.

The chemical formulas of the tetrazolium salt (A) are shown below.

[Formula 6]

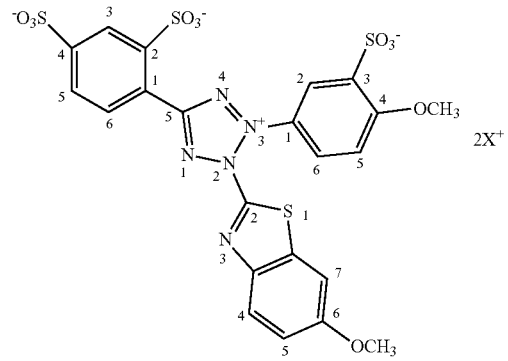

wherein X is Na.

The content of the chromogenic indicator in the reagent layer 30 may be appropriately selected depending on the desired blood glucose level measuring range. For example, in order to accurately measure a wide blood glucose level of 0 mg/dL to 1200 mg/dL, the concentration of coating liquid can be 17 mmol/L or more, for example, 17.3 mmol/L to 55.6 mmol/L. In order to accurately measure a wide blood glucose level of 0 mg/dL to 600 mg/dL, the coating liquid is combined in the concentration of, for example, 8.7 mmol/L or more, for example, 8.7 mmol/L to 28 mmol/L.

When the content of the chromogenic indicator is within one of the above exemplary ranges, the absorbance according to the blood glucose level at a wide concentration can be precisely measured. Furthermore, the production efficiency is improved, when the blood glucose level measuring reagent is applied to the blood glucose level measuring chip.

When the total mole number of the chromogenic indicator included in the blood glucose level measuring reagent of the reagent layer 30 is D (mmol) and the volume of the measurement part (reagent part) is B (L), the ratio D/B can be 25.0 mmol/L to 540 mmol/L, for example, 25.0 mmol/L to 160.4 mmol/L.

When the ratio D/B is within the exemplary range, the absorbance may be precisely measured for the blood glucose level at a wide concentration.

—Electron Acceptor (Mediator)—

For example, the electron acceptor (mediator) has a function that (ii) enzyme accepts an electron from the glucose and transfers it to the chromogenic indicator, etc., by (i) accelerating the reaction between the enzyme and glucose in the blood. If desired, the electron acceptor may be appropriately added to a blood glucose level measuring reagent.

The electron acceptor is not particularly limited and may be appropriately selected depending on the purpose. The electron acceptor may be selected from 5-methyl phenazinium methyl sulfate (PMS), 1-methoxy-5-methyl phenazinium methyl sulfate (mPMS), NAD, FAD, PQQ, potassium ferricyanide and the like. These may be used alone or in combination with two or more kinds.

Among these, 1-methoxy-5-methyl phenazinium methyl sulfate (mPMS) is exemplary in that it is excellent in both reactivity and stability.

—Transition Metal Salt—

For example, when the chromogenic indicator is a tetrazolium salt, a chelate complex may be produced by causing a transition metal salt (transition metal ion) and a tetrazolium salt to react with a chelate of each other to develop color. The transition metal salt is not particularly limited as long as it can generate ions in an aqueous liquid (e.g., water, buffer solution, blood, and body fluids), and may be appropriately selected depending on the purpose, but chlorides, bromides, nitrates, sulfate, and organic acid salts with nickel or cobalt are exemplary.

(Blood Glucose Level Measuring Device Set)

Next, a blood glucose level measuring device set as an exemplary embodiment of the present disclosure will be described.

The blood glucose level measuring device set according to an embodiment of the present disclosure includes the blood glucose level measuring chip described above and a blood glucose level measuring device which is attached with the blood glucose level measuring chip, and measures the glucose content in the blood.

Hereinafter, an exemplary blood glucose level measuring device set including a transmission type of a blood glucose level measuring device for measuring light transmitted through a reaction product between the blood and the blood glucose level measuring reagent will be described. The present disclosure is not limited thereto and also provided are a blood glucose level measuring device set having a blood glucose level measuring device for measuring light absorbed by a reaction product, and a reflection type of blood glucose level measuring device for measuring light reflected from the reaction product.

Figure 4:
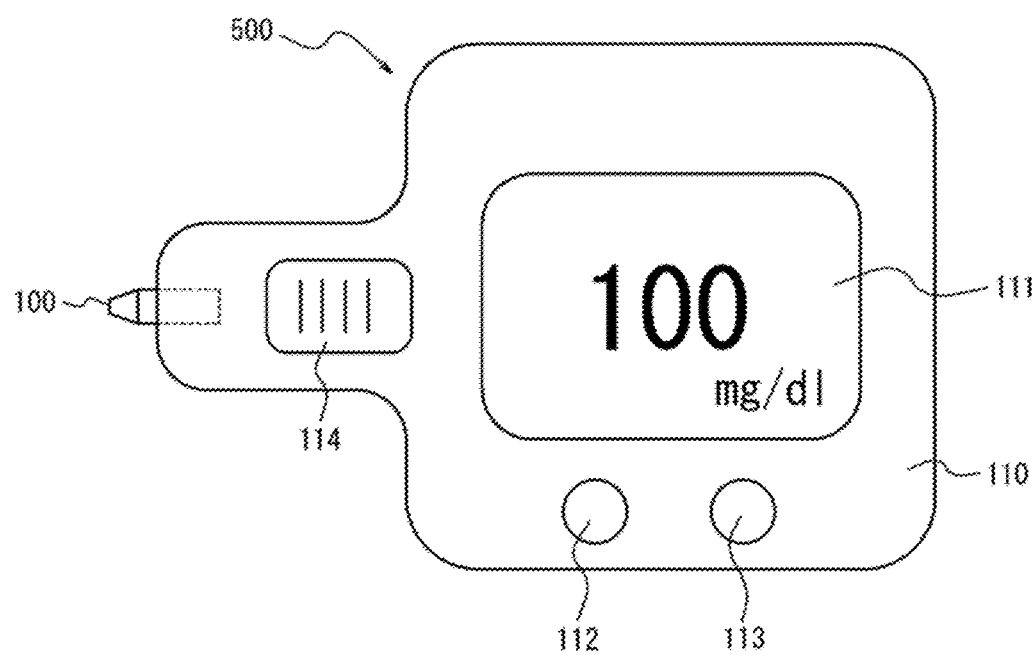
FIG. 4 is a plan view showing a blood glucose level measuring device set according to an exemplary embodiment of the present disclosure.

FIG. 4 is a view for describing a blood glucose level measuring device set 500 according to an exemplary embodiment of the present disclosure. The blood glucose level measuring device set 500 includes a blood glucose level measuring device 110 and a blood glucose level measuring chip 100. The blood glucose level measuring chip 100 is attached to the tip of the blood glucose level measuring device 110. The blood glucose level measuring device 110 includes a display 111 for displaying a measurement result and contents of an operation, a power button 112 for instructing start and stop of the blood glucose level measuring device 110, an operation button 113, and a releasing lever 114 for separating the blood glucose level measuring chip 100 from each other. The display 111 is composed of a liquid crystal, an LED, or the like. The blood glucose level measuring device 110 may be capable of communicating with an external device.

Figure 5:
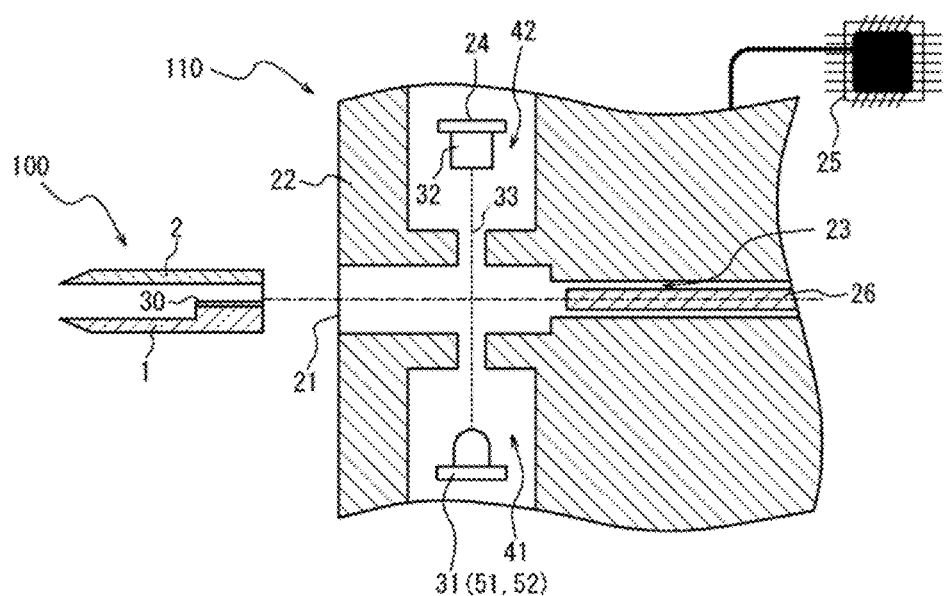
FIG. 5 is a longitudinal cross-sectional view representing a blood glucose level measuring device and a blood glucose level measuring chip of the blood glucose level measuring device set shown in FIG. 4.

FIG. 5 is a vertical sectional view showing the tip of the blood glucose level measuring device 110 and the blood glucose level measuring chip 100 of the blood glucose level measuring device set 500 individually. The mounting part 22 having the opening 21 formed at the tip of the blood glucose level measuring device 110 is installed in the blood glucose level measuring device 110 for attaching the chip 100 so that the blood glucose level measuring device 110 can measure the blood glucose level and mounting pore 23 for attaching the chip 100 is defined. In addition, an optical measuring part 24 for measuring the glucose component (blood glucose level) of blood collected in the blood glucose level measuring chip 100 is installed in the blood glucose level measuring device 110. In addition, the blood glucose level measuring device 110 includes a processing section 25 for processing a signal obtained from the measurement light to calculate a blood glucose level and an ejection pin 26 in association with the releasing lever 114 (see FIG. 4) to separate the blood glucose level measuring chip 100. Hereinafter, each configuration will be described.

At the time of measurement, first, the blood glucose level measuring chip 100 is attached to the mounting pore 23. The attaching operation is manually performed by the user. Although it is not shown, a locking mechanism or the like for fixing the blood glucose level measuring chip 100 to a predetermined position of the mounting pore 23 can be provided so as to minimize imbalance in mounting position caused by a manual operation.

The optical measuring part 24 includes an irradiation part 31 for irradiating an object to be detected with light and a light (for example, light absorbed by the detection target or light reflected from the detection target) transmitted through the detection target and a light receiving part 32 for receiving the light as measurement light. In an exemplary embodiment, a light emitting diode (LED) is used as the irradiation part 31, but a halogen lamp, a laser, or the like may be used. For example, a photodiode (PD) is used for the light receiving part 32. The light receiving part 32 may be a CCD, a CMOS, or the like as long as it can convert received light into a predetermined signal. In addition, the detection target may include any one of a blood component, a reaction product between the blood and the blood glucose level measuring reagent, a reaction intermediate, and the blood glucose level measuring reagent unreacted with the blood, as well as a chromogenic indicator product to be measured.

In an exemplary embodiment, the irradiation part 31 includes at least a first light emitting element 51 that emits light having a first wavelength and a second light emitting element 52 that emits light having a second wavelength that is different from the first wavelength. For example, the first wavelength is a wavelength for detecting the degree of developing a color depending on the blood glucose level, and is, for example, in the wavelength range of 600 to 900 nm. The second wavelength is a wavelength for detecting a concentration of red blood cell in the blood, and is, for example, in the wavelength range of 510 to 590 nm. Furthermore, the irradiation part 31 may further include a light emitting element according to the purpose.

The arrangement of the irradiation part 31 and the light receiving part 32, and an exemplary positional relationship between them will be described. In the 0blood glucose level measuring device 110, a first space 41 and a second space 42 are formed. The irradiation part 31 is disposed in the first space 41 and the light receiving part 32 is disposed in the second space 42. The first space 41 and the second space 42 are opposed to each other with the mounting pore 23 therebetween (see FIG. 5) in a state where the blood glucose level measuring chip 100 is not attached on the blood glucose level measuring device 110. The first space 41 and the second space 42 are placed at a position where the reagent layer 30 on the blood glucose level measuring chip 100 is held in a state where the blood glucose level measuring chip 100 is attached on the blood glucose level measuring device 110, respectively. In order to make a length of the light path constant, it is preferable that the irradiation part 31 be placed at a position where the irradiation light 33 can vertically irradiate the bottom surface of the blood glucose level measuring chip 100 when the irradiation part 31 optically measures the measuring part of the blood glucose level measuring chip 100.

Although it is not shown, when a halogen lamp for irradiating white light is used as the irradiation part 31, a spectroscopic filter may be provided to extract only a specific wavelength as the irradiation light 33. Furthermore, in order to effectively perform irradiation with low energy, a method of providing a condenser lens can be used.

Hereinafter, the present disclosure will be described in more detail with reference to examples, but the present disclosure is not limited to the following examples.

EXAMPLE

Example 1

<Preparation of Reagent Aqueous Solution (Coating Liquid)>

First, glucose dehydrogenase (FAD-GDH) 10 (MU/L: mega unit/liter) to 11 (MU/L: mega unit/liter) as an enzyme, and 64.1 mmol/L of a 1,3-benzene disulfonic acid disodium, sulfonate (DSB, manufactured by Alfa Aear) as the reaction promoter (aromatic hydrocarbon), and 56 mmol/L of tetrazolium salt (A) (material name: 2-(6-methoxybenzothiazolyl)-3-(3-sulfo-4-methoxy-phenyl)-5-(2,4-disulfophenyl)-2H-tetrazolium salt manufactured by Terumo corporation) as the chromogenic indicator, 207 mmol/L of nickel ion as a chelating agent, and an aqueous solution of sodium hydroxide as a pH adjusting agent (an appropriate amount) pH 6.5 to 7) was prepared.

<Production of Blood Glucose Level Measuring Chip>

Prepared reagent aqueous solution was applied onto a polyethylene terephthalate (PET) film 40 (manufactured by Toray Industries Inc, Product name: Lumirror T60, thickness 188 μm, 8 mm×80 mm) placed on the table by an inkjet (Labojet-500Bio manufacured by MICROJET corporation) with patterning accuracy of within±5 μm and a discharge liquid amount of 1 pL to 1000 pL, and dried at 25° C. for 10 minutes. After drying, the PET film 40 on which the reagent layer 30 is formed was cut into a predetermined size to produce a film piece 40a (see FIG. 6(a)). In this film piece 40a, 0.6489 μL of coating liquid was applied per one piece. To this film piece 40a, 23.8 μg of organic acid nickel, 25.0 μg of chromogenic indicator (tetrazolium salt (A)), 8.6 μg of FAD-GDH (803 U/mg) and 11.7 μg of DSB were applied. In addition, the reagent mass per chip for measuring blood glucose level was calculated from the mass of each reagent component added at the time of preparing the coating liquid and the final volume (188 μL) of the prepared coating liquid.

On both sides of a hydrophilized polyester film (3M Company, trade name: hydrophilized polyester film 9901P, thickness: 100 μm), film piece 40a was attached so that the reagent layer 30 faces the chip base 70 and is the center of the flow path 20 on the chip base 70 0on which Double-sided tape (NITTO DENKO CORPORATION, trade name: 5605BN, thickness: 50 μm) was formed as the spacer and the adhesive parts 3 and 4 (see FIG. 6(b)). When the film piece 40a is attached, the film piece 40a was pressed so as to be inserted into a double-sided tape in a predetermined amount. In addition, a double-sided tape (manufactured by 3M Company, trade name: polyester film base, double-faced adhesive tape 9965, thickness: 80 μm) was attached to the above-mentioned hydrophilic polyester film on the chip base 70 to which the film piece 40a was attached, and the blood glucose level measuring chip 100 shown in FIGS. 1, 2 and 3 was fabricated by covering the film pieces 40b (see FIGS. 6(c) and 6(d)).

In this case, the total mole number A of the aromatic hydrocarbons contained in the reagent layer 30 of the manufactured blood glucose level measuring chip 100 was 0.041×10-3 (mmol).

The manufactured blood glucose level measuring chip 100 has the flow path part 20a and the measuring part (reagent part) 20b (FIG. 3). In the flow path part 20a, the flow path length L1 was 9 mm, the width W was 1.5 mm, and the thickness t1 was 0.13 mm. In the measuring part 20b, the reagent length L2 was 3 mm, the width W was 1.5 mm, the thickness t2 was 0.05 mm, and the volume B was $0.225 \times 10^{-6}$ (L). In this case, the volume of the measurement portion is determined by, on the inner walls defining the flow path 20, the reagent formed surface 1a on which the reagent layer 30 made of the blood glucose level measuring reagent is formed, and the opposing surface 2a facing the reagent layer 30 in the thickness direction of the reagent layer 30 and is the volume B of the gap X (that is, the region X in which the blood glucose level measuring reagent and the blood are dissolved) sandwiched by the reagent formed surface 1a and the opposing surface 2a. From the above, the A/B ratio was 184.8 mmol/L.

<Preparation of Blood Samples>

A blood sample (BG100) having 100 mg/dL of a glucose concentration (BG) was prepared by adding a high concentration glucose solution (40 g/dL) to blood (whole blood, hematocrit value (Ht) 40). As a control, a blood sample (BG0) having 0 mg/dL of a glucose concentration (BG) was prepared by adding an enzyme decomposing the glucose to blood (whole blood, hematocrit value (Ht) 40).

<Evaluation of Blood Spreading>

3 mm$^3$ of the prepared blood sample was adhered to the manufactured blood glucose level measuring chip, and blood spreading evaluation was carried out visually according to the following evaluation criteria. The results are shown in Table 1. The ambient temperature was 5° C. (low temperature condition), 25° C. (normal temperature condition) and 40° C. (high temperature condition).

<<Evaluation Criteria>>

○: Good (uniformly spreading without generating any air bubbles)

Δ: Permissible range (air bubbles are slightly generated)

×: poor (bubbles, a void area occurs)

<Evaluation of the Reaction Rate>

The absorbance measurement (measurement wavelength: 650 nm and 900 nm) was performed using an ultraviolet visible spectrophotometer in a state wherein 3 mm$^3$ of the prepared blood sample was adhered to the manufactured blood glucose level measuring chip and the blood glucose level measuring reagent was dissolved in the blood sample, and then the reaction rate was evaluated according to the evaluation criteria as described below. The results are shown in Table 1 and FIG. 7.

FIG. 7 is a graph showing the color development rate, wherein the vertical axis represents the absorbance index (the amount of net color development when the net color development amount after 15 seconds is 100%) and the horizontal axis represents the time (sec). Also, for example, the "net color development amount" refers to the amount of blood at a blood glucose level of 0 mg/dL from the absorbance when blood of a desired blood glucose level (for example, 100 mg/mL) is reacted with a blood glucose level measuring reagent in blood of the same hematocrit value, and it is the amount of net color development, minus the absorbance when reacted with the blood glucose level measuring reagent. The absorbance used in the calculation of the coloring amount was a value obtained by subtracting the absorbance at 900 nm from the absorbance at 650 nm in order to correct the optical unbalance other than the coloring. The absorbance at 650 nm includes the amount of coloring derived from glucose and noise due to scattered light. The absorbance at 900 nm reflects the amount of noise at 650 nm due to scattered light.

<<Evaluation Criteria>>

○: Good (Absorbance index after 9 seconds is 90% or more when the absorbance index after 15 seconds from the start of reaction is taken as 100%. The starting point of the reaction was specified by detecting the reagent filled with blood by image analysis.

×: Poor (other than good(○))

Example 2

The preparation of a reagent aqueous solution (coating liquid), a blood glucose level measuring chip, and a blood sample, and evaluation of blood spreading and reaction rate were carried out in a manner similar to those described in Example 1 except that the concentration of DSB (concentration of DSB coating liquid) as a reaction promoter (aromatic hydrocarbon) in the reagent aqueous solution was 21.4 mmol/L and the A/B ratio was 61.6 mmol/L. The evaluation results are shown in Table 1 and FIG. 7.

Example 3

The preparation of a reagent aqueous solution (coating solution), a blood glucose level measuring chip, and a blood sample, and evaluation of blood spreading and reaction rate were carried out in a manner similar to those described in Example 1 except that the concentration of DSB (concentration of DSB coating liquid) as a reaction promoter (aromatic hydrocarbon) in the reagent aqueous solution was 10.7 mmol/L and the A/B ratio was 30.8 mmol/L. The evaluation results are shown in Table 1 and FIG. 7.

Example 4

The preparation of a reagent aqueous solution (coating liquid), a blood glucose level measuring chip, and a blood sample, and evaluation of blood spreading and reaction rate were carried out in a manner similar to those described in Example 1, except that the A/B ratio value of reagent aqueous solution (coating liquid) has A/B ratio of each component as measured by the following measurement method, respectively as DSB: 15.0 mmol/L, tetrazolium salt A (chromogenic indicator): 50 mmol/L, nickel ion: 250 mmol/L, and FAD-GDH: 11.2 (MU/L). Furthermore, a DSB concentration of the reagent aqueous solution (coating liquid) was 1.3 mmol/L. The evaluation results are shown in Table 1 and FIG. 7.

When the absorbance after 15 seconds was taken as 100%, the absorbance after 9 seconds was 97.3%.

<Measurement Method of Ratio A/B Value>

1,000 μL of RO water was accurately added to the chip of which the fabrication was completed to dissolve the blood glucose level measuring reagent and recover the aqueous solution. The solution was quantified as a sample solution with UPLC (Super High Speed Separation Liquid Chromatography SHIMAZU NEXERA X2, manufactured by Shimadzu Corporation).

Next, the concentration of the chromogenic indicator in the sample liquid was obtained from the quantification result by the UPLC.

Also, the concentration of the coloring reagent is calculated when RO water (glucose concentration: 0 mg water) flows into the space (volume B (L)) of the region in which the measuring reagent and blood are dissolved.

Furthermore, for each component other than the chromogenic indicator, calculation was made based on the composition of the coating liquid (concentration ratio of each component) of the measuring reagent.

Example 5

Preparation of the reagent aqueous solution (coating liquid), a blood glucose level measuring chip, a blood sample, and evaluation of blood spreading, and the reaction rate were carried out in the manner similar to those in Example 4, except that an reagent aqueous solution (coating liquid) was prepared so that the A/B ratio of the DSB measured by the above measuring method was 7.5 mmol/L. Furthermore, DSB concentration of the reagent aqueous solution (coating liquid) was 2.6 mmol/L. The evaluation results are shown in Table 1 and FIG. 7.

Furthermore, when the absorbance after 15 seconds was taken as 100%, the absorbance after 9 seconds was 95.8%.

Example 6

Preparation of the reagent aqueous solution (coating liquid), a blood glucose level measuring chip, and a blood sample, and evaluation of blood spreading, and evaluation of the reaction rate were carried out in the manner similar to those in Example 4, except that an reagent aqueous solution (coating liquid) was prepared so that the A/B ratio of the DSB measured by the above measuring method was 3.75 mmol/L. Furthermore, DSB concentration of the reagent aqueous solution (coating liquid) was 5.2 mmol/L. The evaluation results are shown in Table 1 and FIG. 7.

When the absorbance after 15 seconds was taken as 100%, the absorbance after 9 seconds was 94.1%.

Comparative Example 1

The preparation of a reagent aqueous solution (coating liquid), a blood glucose level measuring chip, and a blood sample, and evaluation of blood spreading and reaction rate were carried out in a manner similar to those described in Example 1 except that the concentration of DSB (concentration of DSB coating liquid) as a reaction promoter (aromatic hydrocarbon) in the reagent aqueous solution was 0 mmol/L and the A/B ratio was 0 mmol/L. The evaluation results are shown in Table 1 and FIG. 7.

Example 7

The preparation of reagent aqueous solution (coating liquid), a blood glucose level measuring chip, and a blood sample, and evaluation of blood spreading and reaction rate were carried out in a manner similar to those described in Example 1, except that the hematocrit value (Ht) was 60. The evaluation results are shown in Table 1.

Example 8

The preparation of a reagent aqueous solution (coating liquid), a blood glucose level measuring chip, and a blood sample, and evaluation of blood spreading and reaction rate were carried out, in a manner similar to those described in Example 7 except that the concentration of DSB (concentration of DSB coating liquid) as a reaction promoter (aromatic hydrocarbon) in the reagent aqueous solution was 42.7 mmol/L and the A/B ratio was 123.2 mmol/L. The evaluation results are shown in Table 1.

Example 9

The preparation of a reagent aqueous solution (coating liquid), a blood glucose level measuring chip, and a blood sample, and evaluation of blood spreading and reaction rate were carried out in a manner similar to those described in Example 7 except that the concentration of DSB (concentration of DSB coating liquid) as a reaction promoter (aromatic hydrocarbon) in the aqueous reagent solution was 21.4 mmol/L and the A/B ratio was 61.6 mmol/L. The evaluation results are shown in Table 1.

Example 10

The preparation of reagent aqueous solution (coating liquid), a blood glucose level measuring chip, and a blood sample, and evaluation of blood spreading and reaction rate were carried out in a manner similar to those described in example 8, except that the hematocrit value (Ht) was 70. The evaluation results are shown in Table 1.

Example 11

The preparation of a reagent aqueous solution (coating liquid), a blood glucose level measuring chip, and a blood sample, and evaluation of blood spreading and reaction rate were carried out in a manner similar to those described in Example 9 except that the concentration of DSB (concentration of DSB coating liquid) as a reaction promoter (aromatic hydrocarbon) in the aqueous reagent solution was 21.4 mmol/L and the A/B ratio was 61.6 mmol/L. The evaluation results are shown in Table 1.

Example 12

The preparation of a reagent aqueous solution (coating liquid), a blood glucose level measuring chip, and a blood sample, and evaluation of blood spreading and reaction rate were carried out in a manner similar to those described in Example 4, except that the hematocrit value (Ht) was 70. The evaluation results are shown in Table 1.

Example 13

The preparation of a reagent aqueous solution (coating liquid), a blood glucose level measuring chip, and a blood sample, and evaluation of blood spreading and reaction rate were carried out in a manner similar to those described in Example 5, except that the hematocrit value (Ht) was 70. The evaluation results are shown in Table 1.

Example 14

The preparation of reagent aqueous solution (coating liquid), a blood glucose level measuring chip, and a blood sample, and evaluation of blood spreading and reaction rate were carried out in a manner similar to those described in Example 6, except that the hematocrit value (Ht) was 70. The evaluation results are shown in Table 1.

Example 15

The preparation of reagent aqueous solution (coating liquid), a blood glucose level measuring chip, and a blood sample, and evaluation of blood spreading and reaction rate were carried out in a manner similar to those described in Example 1, except that the hematocrit value (Ht) was 20. The evaluation results are shown in Table 1.

Example 16

The preparation of reagent aqueous solution (coating liquid), a blood glucose level measuring chip, and a blood sample, and evaluation of blood spreading and reaction rate were carried out in a manner similar to those described in Example 1, except that the hematocrit value (Ht) was 0. The evaluation results are shown in Table 1.

Example 17

The preparation of reagent aqueous solution (coating liquid), a blood glucose level measuring chip, and a blood sample, and evaluation of blood spreading and reaction rate were carried out in a manner similar to those described in Example 1, except that the concentration of the blood glucose (BG) in a sample was 400 mg/dL. The evaluation results are shown in Table 1.

Example 18

The preparation of reagent aqueous solution (coating liquid), a blood glucose level measuring chip, and a blood sample, and evaluation of blood spreading and reaction rate were carried out in a manner similar to those described in Example 1, except that the concentration of the blood glucose in a sample was 800 mg/dL. The evaluation results are shown in Table 1.

Example 19

The preparation of reagent aqueous solution (coating liquid), a blood glucose level measuring chip, and a blood sample, and evaluation of blood spreading and reaction rate were carried out in a manner similar to those described in example 18, except that trisodium naphthalene -1,3,6- tri sulfonate (TSN, Tokyo chemical industry co., Ltd) was used instead of the preparation of the reagent aqueous solution using DSB as the reaction promoter (aromatic hydrocarbon) in the reagent aqueous solution The evaluation results are shown in Table 1.

TABLE 1

| Sample | | Concentration of DSB coating liquid | A/B ratio | Concentration of DSB (mmol/L) in | Reaction rate | Spreading | | |
|---|---|---|---|---|---|---|---|---|
| Ht | BG | (mM) | (mmol/L) | plasma | | 5° C. | 25° C. | 40° C. |
| Example 1 | 40 | 100 | 64.1 | 184.8 | 308.0 | ○ | ○ | ○ | ○ |
| Example 2 | 40 | 100 | 21.4 | 61.6 | 102.7 | ○ | ○ | ○ | ○ |
| Example 3 | 40 | 100 | 10.7 | 30.8 | 51.3 | ○ | ○ | ○ | ○ |
| Example 4 | 40 | 100 | — | 15.0 | 25.0 | ○ | ○ | ○ | ○ |
| Example 5 | 40 | 100 | — | 7.5 | 12.5 | ○ | ○ | ○ | ○ |
| Example 6 | 40 | 100 | — | 3.75 | 5.25 | ○ | ○ | ○ | ○ |
| Comparative Example 1 | 40 | 100 | 0 | 0 | 0 | X | ○ | ○ | ○ |
| Example 7 | 60 | 100 | 64.1 | 184.8 | 462.0 | ○ | ○ | ○ | X |
| Example 8 | 60 | 100 | 42.7 | 123.2 | 308.0 | ○ | ○ | ○ | ○ |
| Example 9 | 60 | 100 | 21.4 | 61.6 | 154.0 | ○ | ○ | ○ | ○ |
| Example 10 | 70 | 100 | 42.7 | 123.2 | 410.7 | ○ | ○ | ○ | X |
| Example 11 | 70 | 100 | 21.4 | 61.6 | 205.3 | ○ | ○ | ○ | X |
| Example 12 | 70 | 100 | — | 15.0 | 50.0 | ○ | ○ | ○ | ○ |
| Example 13 | 70 | 100 | — | 7.5 | 25.0 | ○ | ○ | ○ | ○ |
| Example 14 | 70 | 100 | — | 3.75 | 12.5 | ○ | ○ | ○ | ○ |
| Example 15 | 20 | 100 | 64.1 | 184.8 | 231.0 | ○ | ○ | ○ | ○ |
| Example 16 | 0 | 100 | 64.1 | 184.8 | 184.8 | ○ | ○ | ○ | ○ |
| Example 17 | 40 | 400 | 64.1 | 184.8 | 308.0 | ○ | ○ | ○ | ○ |
| Example 18 | 40 | 800 | 64.1 | 184.8 | 308.0 | ○ | ○ | ○ | ○ |
| Example 19 | 40 | 800 | TSN 64.1 | 184.8 | TSN 308.0 | ○ | ○ | ○ | ○ |

Examples 1 to 19 using a blood glucose level measuring chip having an A/B ratio of 3.7 mmol/L to 184.8 mmol/L, and comparative example 1 using the blood glucose level measuring chip out of an A/B ratio of 3.7 mmol/L to 184.8 mmol/L were compared, and it was found that the blood glucose level measuring chip having the A/B ratio of 3.7 mmol/L to 184.8 mmol/L was excellent in a compatibility of the blood with the blood glucose level measuring reagent, and could maintain the reaction rate of the blood with the blood glucose level measuring reagent. By using a blood glucose level measuring chip with the A/B ratio of 3.7 mmol/L to 123.3 mmol/L, the reaction rate between the blood and the blood glucose level measuring reagent could be maintained while further increasing the compatibility. The use of a blood glucose level measuring chip having an A/B ratio of 3.7 mmol/L to 61.6 mmol/L makes it possible to improve the reaction rate between the blood and the blood glucose level measuring reagent, even in a case where the blood generally has a high hematocrit. By using a blood glucose level measuring chip having an A/B ratio of 3.7 mmol/L to 15.0 mmol/L, the blood having a high hematocrit value was excellent in the compatibility and could maintain the reaction rate of the blood with the blood glucose level measuring reagent.

As described above, even in a case where the blood having a high hematocrit value (Ht) is supplied to the blood glucose level measuring chip, the blood glucose level measuring reagent, the blood glucose level measuring chip and the blood glucose level measuring set of the present disclosure could control the generation of air bubbles in the flow path since it is difficult to induce the imbalance of the mixing and dissolution rate of the blood with the blood glucose level measuring reagent (the blood and the blood glucose level measuring reagent were excellent in the compatibility). Furthermore, when the blood glucose level is measured, the blood with the blood glucose level measuring reagent could be rapidly reacted and be detected. In other words, in the blood glucose measurement chip wherein the blood glucose level measuring reagent is in a dry state, the blood glucose level measuring reagent can be rapidly dissolved in the blood, irrespective of the hematocrit value or the environmental temperature of the inflowing blood, while increasing the inflowing rate, and the blood and the blood glucose level measuring reagent could be uniformly mixed. Furthermore, the reaction rate of the blood with the blood glucose level measuring reagent was good. As described above, the rapid and precise blood glucose level could be measured.

Industrial Applicability

Exemplary aspects of the present disclosure relate to a blood glucose level measuring chip and blood glucose level measuring device set, and in particular, a blood glucose level measuring chip which is excellent in blood spreading and may maintain a reaction rate of blood with a reagent, even in a case where the blood with a high hematocrit value (Ht) is supplied, and the blood glucose level measuring device set including the blood glucose level measuring chip.

REFERENCE SIGNS LIST

1 First base
1a Reagent formed surface
2 Second base
2a Opposing surface
3 Adhesive part
4 Adhesive part
10 Supply port
20 Flow path
20a Flow path part
20b Measuring part (reagent part)
21 Opening part
22 Mounting part
23 Mounting pore
24 Optical measuring part
25 Processing section 26 Ejection pin
30 Reagent layer (reagent)
31 Irradiation part
32 Light receiving part
33 Irradiation light
40 PET film
40a Film piece
40b Film piece
41 First space
42 Second base
51 First emitting element
52 Second emitting element
70 Chip base
100 Blood glucose level measuring chip
110 Blood glucose level measuring device
111 Display
112 Power button
113 Operation button
114 Releasing lever
500 Blood glucose level measuring device set
X Gap (region)
t1 Thickness
t2 Thickness
L1 Length of flow path
L2 Length of reagent
W Width
Y Space

What is claimed is:

1. A blood glucose level measuring chip attachable on a blood glucose level measuring device of a blood glucose level in blood, the chip comprising:
a supply port through which the blood is supplied;
a flow path having the supply port formed at one end of the flow path; and
a blood glucose level measuring reagent disposed on an inner wall defining the flow path,
wherein the blood glucose level measuring reagent contains an aromatic hydrocarbon having at least one sulfonic acid group, and
an A/B ratio is in a range of 3.7 mmol/L to 184.8 mmol/L, wherein A (in mmol) represents a total molar number of aromatic hydrocarbons contained in the blood glucose level measuring reagent, and B (in L) represents a volume of a region in which the blood glucose level measuring reagent and the blood are mixed or the reagent is dissolved in the blood, wherein the region consists of a gap between a surface on which the reagent layer is formed and an opposing surface facing the reagent layer in the thickness direction of the reagent layer, on the inner wall defining the flow path, wherein the volume of the region is calculated as follows:

$$\text{volume of the region} = (\text{reagent length } L2) \times (\text{width } W) \times (\text{thickness } t2)$$

wherein the reagent length L2 consists of a length of the blood glucose level measuring reagent, the width W consists of a width of the gap between the surface on which the reagent layer is formed and the opposing surface facing the reagent layer in the thickness direction of the reagent layer, such that the width is the total width of the flow path, and the thickness t2 consists of a thickness of the gap between the surface on which the reagent layer is formed and the opposing surface facing the reagent layer in the thickness direction of the reagent layer.

2. The blood glucose level measuring chip according to claim 1, wherein the A/B ratio is in a range of 3.7 mmol/L to 123.3 mmol/L.

3. The blood glucose level measuring chip according to claim 2, wherein the A/B ratio is in a range of 3.7 mmol/L to 61.6 mmol\L.

4. The blood glucose level measuring chip according to claim 3, wherein the A/B ratio is in a range of 3.7 mmol/L to 15.0 mmol/L.

5. The blood glucose level measuring chip according to claim 1, wherein the aromatic hydrocarbon has two or more sulfonic acid groups.

6. The blood glucose level measuring chip according to claim 5, wherein the aromatic hydrocarbon is disodium 1,3-benzene disulfonate, or trisodium naphthalene-1,3,6-trisulfonate.

7. The blood glucose level measuring chip according to claim 1, wherein the blood glucose level measuring reagent further contains an enzyme having glucose as a substrate and a chromogenic indicator.

8. The blood glucose level measuring chip according to claim 7, wherein the blood glucose level measuring reagent contains the aromatic hydrocarbon in a range of 1 pmol to 12 pmol per 1 U of the enzyme.

9. The blood glucose level measuring chip according to claim 7, wherein in the blood glucose level measuring reagent, a mole ratio of the chromogenic indicator to the aromatic hydrocarbon is in a range of 1:0.07 to 1:7.4.

10. The blood glucose level measuring chip according to claim 7, wherein the chromogenic indicator includes a tetrazolium salt.

11. The blood glucose level measuring chip according to claim 7, wherein the enzyme includes glucose dehydrogenase or glucose oxidase.

12. The blood glucose level measuring chip according to claim 1, wherein the amount of the aromatic hydrocarbon contained in the blood glucose level measuring reagent is in a range of 0.238 to 11.7 μg per chip, wherein the aromatic hydrocarbon is a disodium salt of the aromatic hydrocarbon, wherein the aromatic hydrocarbon is measured as a disodium salt of the aromatic hydrocarbon.

13. The blood glucose level measuring chip according to claim 1, wherein the amount of the aromatic hydrocarbon contained in the blood glucose level measuring reagent is in a range of 0.238 to 0.952 μg per chip, wherein the aromatic hydrocarbon is a disodium salt of the aromatic hydrocarbon, wherein the aromatic hydrocarbon is measured as a disodium salt of the aromatic hydrocarbon.

14. The blood glucose level measuring chip according to claim 1, wherein the volume of the flow path is in a range of 0.0003 to 0.003 cm$^3$.

15. The blood glucose level measuring chip according to claim 1, wherein the volume of the flow path is in a range of 0.00005 to 0.0003 cm$^3$.

16. The blood glucose level measuring chip according to claim 1, wherein the blood glucose level measuring reagent only partially covers the total inner surface of the flow path.

17. The blood glucose level measuring chip according to claim 1, wherein the inner wall on which the blood glucose level measuring reagent is disposed faces an opposing inner wall, wherein the blood glucose level measuring reagent is not disposed on the opposing inner wall.

18. The blood glucose level measuring chip according to claim 1, wherein at least a portion of the blood glucose level measuring reagent is disposed at an end of the flow path that is opposite the end at which the supply port is formed.

19. The blood glucose level measuring chip according to claim 1, wherein the cross-sectional shape of the flow path is a circle or an ellipse.

20. A blood glucose level measuring device set comprising:
- the blood glucose level measuring chip according to claim 1; and
- a blood glucose level measuring device for measuring a blood glucose level in blood,
- wherein the blood glucose level measuring device comprises an irradiation part for irradiating a reaction product of the blood and the reagent with light, and
- a light receiving part for receiving measurement light transmitted through the reaction product, measurement light absorbed by the reaction product, or measurement light reflected from the reaction product, and
- a processing section for processing a signal obtained from the measurement light.

* * * * *